US011603395B2

(12) United States Patent
Baileykobayashi et al.

(10) Patent No.: US 11,603,395 B2
(45) Date of Patent: Mar. 14, 2023

(54) ANTITUMOR PEPTIDE AND USE THEREOF

(71) Applicant: TOAGOSEI CO., LTD, Tokyo (JP)

(72) Inventors: Nahoko Baileykobayashi, Tsukuba (JP); Tetsuhiko Yoshida, Tsukuba (JP)

(73) Assignee: TOAGOSEI CO., LTD, Tokyo (JP)

( * ) Notice: Subject to any disclaimer, the term of this patent is extended or adjusted under 35 U.S.C. 154(b) by 285 days.

(21) Appl. No.: 16/889,020

(22) Filed: Jun. 1, 2020

(65) Prior Publication Data
US 2020/0407412 A1 Dec. 31, 2020

(30) Foreign Application Priority Data

Jun. 25, 2019 (JP) .............................. JP2019-116906

(51) Int. Cl.
*C07K 14/52* (2006.01)
*A61P 35/00* (2006.01)
*A61K 38/00* (2006.01)
*C07K 14/00* (2006.01)

(52) U.S. Cl.
CPC ............ *C07K 14/521* (2013.01); *A61P 35/00* (2018.01); *C07K 14/001* (2013.01); *A61K 38/00* (2013.01)

(58) Field of Classification Search
CPC ........ C07K 14/521; A61P 35/00; A61K 38/00
See application file for complete search history.

(56) References Cited

U.S. PATENT DOCUMENTS

| 2003/0050466 A1* | 3/2003 | Ni | A61P 7/02 |
| | | | 435/325 |
| 2006/0110383 A1 | 5/2006 | Honjo et al. | |
| 2010/0297758 A1* | 11/2010 | Yoshida | C12N 15/625 |
| | | | 435/325 |

FOREIGN PATENT DOCUMENTS

WO 2004004771 A1 1/2004

OTHER PUBLICATIONS

Goyal et al., 2006, Phosphorylation-dependent Regulation of Unique Nuclear and Nucleolar Localization Signals of LIM Kinase 2 in Endothelial Cells, The Journal of Biological Chemistry, 281(35):25223-25230.*
Mezzadra, Ricardo et al. "Identification of CMTM6 and CMTM4 as PD-L1 protein regulators." Nature, vol. 549, No. 7670, 2017, pp. 106-110, 39 pages (supplemental figures).
Imamovic, Denira, et al. "Novel regulators of PD-L1 expression in cancer: CMTM6 and CMTM4—a new avenue to enhance the therapeutic benefits of immune checkpoint inhibitors." Annals of Translational Medicine, vol. 5, No. 23, 2017, p. 467, 3 pages.

* cited by examiner

*Primary Examiner* — Amber D Steele
(74) *Attorney, Agent, or Firm* — Occhiuti & Rohlicek LLP

(57) ABSTRACT

A synthetic peptide provided according to the technology disclosed here includes
(1) a CMTM4-TM related sequence; and
(2) an amino acid sequence that functions as a cell membrane permeable peptide.
The synthetic peptide has a total number of amino acid residues of 100 or less.

8 Claims, No Drawings
Specification includes a Sequence Listing.

```
                     SEQUENCE LISTING

<160> NUMBER OF SEQ ID NOS: 47

<210> SEQ ID NO 1
<211> LENGTH: 21
<212> TYPE: PRT
<213> ORGANISM: Artificial Sequence
<220> FEATURE:
<223> OTHER INFORMATION: synthetic peptide

<400> SEQUENCE: 1

Val Ala Gln Val Ile Leu Ala Leu Ile Ala Phe Ile Cys Ile Glu Thr
1               5                   10                  15

Ile Met Ala Cys Ser
            20

<210> SEQ ID NO 2
<211> LENGTH: 21
<212> TYPE: PRT
<213> ORGANISM: Artificial Sequence
<220> FEATURE:
<223> OTHER INFORMATION: synthetic peptide

<400> SEQUENCE: 2

Tyr Phe Phe Glu Phe Val Ser Cys Ser Ala Phe Val Val Thr Gly Val
1               5                   10                  15

Leu Leu Ile Met Phe
            20

<210> SEQ ID NO 3
<211> LENGTH: 21
<212> TYPE: PRT
<213> ORGANISM: Artificial Sequence
<220> FEATURE:
<223> OTHER INFORMATION: synthetic peptide

<400> SEQUENCE: 3

Leu Val Asn Thr Gly Leu Ser Ala Phe Leu Phe Phe Ile Ala Ser Ile
1               5                   10                  15

Val Leu Ala Ala Leu
```

```
<210> SEQ ID NO 4
<211> LENGTH: 21
<212> TYPE: PRT
<213> ORGANISM: Artificial Sequence
<220> FEATURE:
<223> OTHER INFORMATION: synthetic peptide

<400> SEQUENCE: 4

Ile Ala Ala Val Ile Phe Gly Phe Leu Ala Thr Ala Ala Tyr Ala Val
1               5                   10                  15

Asn Thr Phe Leu Ala
            20

<210> SEQ ID NO 5
<211> LENGTH: 21
<212> TYPE: PRT
<213> ORGANISM: Artificial Sequence
<220> FEATURE:
<223> OTHER INFORMATION: synthetic peptide

<400> SEQUENCE: 5

Val Ala Gln Val Ile Leu Ala Leu Ile Ala Phe Ile Cys Ile Glu Thr
1               5                   10                  15

Ile Met Glu Cys Ser
            20

<210> SEQ ID NO 6
<211> LENGTH: 21
<212> TYPE: PRT
<213> ORGANISM: Artificial Sequence
<220> FEATURE:
<223> OTHER INFORMATION: synthetic peptide

<400> SEQUENCE: 6

Tyr Phe Phe Glu Phe Val Ser Cys Ser Ala Phe Val Val Thr Gly Val
1               5                   10                  15

Leu Leu Ile Leu Phe
            20

<210> SEQ ID NO 7
<211> LENGTH: 21
<212> TYPE: PRT
<213> ORGANISM: Artificial Sequence
<220> FEATURE:
<223> OTHER INFORMATION: synthetic peptide

<400> SEQUENCE: 7

Leu Val Asn Thr Gly Leu Ser Thr Phe Phe Phe Phe Ile Ala Ser Ile
1               5                   10                  15

Val Leu Ala Ala Leu
            20

<210> SEQ ID NO 8
<211> LENGTH: 21
<212> TYPE: PRT
<213> ORGANISM: Artificial Sequence
<220> FEATURE:
<223> OTHER INFORMATION: synthetic peptide

<400> SEQUENCE: 8

Ile Ala Ala Val Ile Phe Gly Phe Leu Ala Thr Ala Ala Tyr Ala Val
1               5                   10                  15
```

Ser Thr Phe Leu Ala
        20

<210> SEQ ID NO 9
<211> LENGTH: 18
<212> TYPE: PRT
<213> ORGANISM: Artificial Sequence
<220> FEATURE:
<223> OTHER INFORMATION: synthetic peptide

<400> SEQUENCE: 9

Val Ala Gln Val Ile Leu Ala Leu Ile Ala Phe Ile Cys Ile Glu Thr
1               5                   10                  15

Ile Met

<210> SEQ ID NO 10
<211> LENGTH: 24
<212> TYPE: PRT
<213> ORGANISM: Artificial Sequence
<220> FEATURE:
<223> OTHER INFORMATION: synthetic peptide

<400> SEQUENCE: 10

Glu Phe Val Ser Cys Ser Ala Phe Val Val Thr Gly Val Leu Leu Ile
1               5                   10                  15

Leu Phe Ser Leu Asn Leu His Met
        20

<210> SEQ ID NO 11
<211> LENGTH: 23
<212> TYPE: PRT
<213> ORGANISM: Artificial Sequence
<220> FEATURE:
<223> OTHER INFORMATION: synthetic peptide

<400> SEQUENCE: 11

Leu Val Asn Thr Gly Leu Ser Thr Phe Phe Phe Phe Ile Ala Ser Ile
1               5                   10                  15

Val Leu Ala Ala Leu Asn His
        20

<210> SEQ ID NO 12
<211> LENGTH: 22
<212> TYPE: PRT
<213> ORGANISM: Artificial Sequence
<220> FEATURE:
<223> OTHER INFORMATION: synthetic peptide

<400> SEQUENCE: 12

Ile Ala Ala Val Ile Phe Gly Phe Leu Ala Thr Ala Ala Tyr Ala Val
1               5                   10                  15

Ser Thr Phe Leu Ala Val
        20

<210> SEQ ID NO 13
<211> LENGTH: 19
<212> TYPE: PRT
<213> ORGANISM: Artificial Sequence
<220> FEATURE:
<223> OTHER INFORMATION: synthetic peptide

<400> SEQUENCE: 13

Val Ala Gln Val Ile Leu Ala Leu Ile Ala Phe Ile Cys Ile Glu Thr
1               5                   10                  15

Ile Met Ala

<210> SEQ ID NO 14
<211> LENGTH: 29
<212> TYPE: PRT
<213> ORGANISM: Artificial Sequence
<220> FEATURE:
<223> OTHER INFORMATION: synthetic peptide

<400> SEQUENCE: 14

Gly Leu Tyr Phe Phe Glu Phe Val Ser Cys Ser Ala Phe Val Val Thr
1               5                   10                  15

Gly Val Leu Leu Ile Met Phe Ser Leu Asn Leu His Met
            20                  25

<210> SEQ ID NO 15
<211> LENGTH: 23
<212> TYPE: PRT
<213> ORGANISM: Artificial Sequence
<220> FEATURE:
<223> OTHER INFORMATION: synthetic peptide

<400> SEQUENCE: 15

Leu Val Asn Thr Gly Leu Ser Ala Phe Leu Phe Phe Ile Ala Ser Ile
1               5                   10                  15

Val Leu Ala Ala Leu Asn His
            20

<210> SEQ ID NO 16
<211> LENGTH: 22
<212> TYPE: PRT
<213> ORGANISM: Artificial Sequence
<220> FEATURE:
<223> OTHER INFORMATION: synthetic peptide

<400> SEQUENCE: 16

Ile Ala Ala Val Ile Phe Gly Phe Leu Ala Thr Ala Ala Tyr Ala Val
1               5                   10                  15

Asn Thr Phe Leu Ala Val
            20

<210> SEQ ID NO 17
<211> LENGTH: 18
<212> TYPE: PRT
<213> ORGANISM: Artificial Sequence
<220> FEATURE:
<223> OTHER INFORMATION: synthetic peptide

<400> SEQUENCE: 17

Val Ala Gln Val Ile Leu Ala Leu Ile Ala Phe Ile Cys Ile Glu Thr
1               5                   10                  15

Ile Met

<210> SEQ ID NO 18
<211> LENGTH: 24
<212> TYPE: PRT
<213> ORGANISM: Artificial Sequence
<220> FEATURE:
<223> OTHER INFORMATION: synthetic peptide

<400> SEQUENCE: 18

Glu Phe Val Ser Cys Ser Ala Phe Val Val Thr Gly Val Leu Leu Ile
1               5                   10                  15

Leu Phe Ser Leu Asn Leu His Met

```
<210> SEQ ID NO 19
<211> LENGTH: 23
<212> TYPE: PRT
<213> ORGANISM: Artificial Sequence
<220> FEATURE:
<223> OTHER INFORMATION: synthetic peptide

<400> SEQUENCE: 19

Leu Val Asn Thr Gly Leu Ser Thr Phe Phe Phe Phe Ile Ala Ser Ile
1               5                   10                  15

Val Leu Ala Ala Leu Asn His
            20

<210> SEQ ID NO 20
<211> LENGTH: 22
<212> TYPE: PRT
<213> ORGANISM: Artificial Sequence
<220> FEATURE:
<223> OTHER INFORMATION: synthetic peptide

<400> SEQUENCE: 20

Ile Ala Ala Val Ile Phe Gly Phe Leu Ala Thr Ala Ala Tyr Ala Val
1               5                   10                  15

Ser Thr Phe Leu Ala Val
            20

<210> SEQ ID NO 21
<211> LENGTH: 19
<212> TYPE: PRT
<213> ORGANISM: Artificial Sequence
<220> FEATURE:
<223> OTHER INFORMATION: synthetic peptide

<400> SEQUENCE: 21

Val Ala Gln Val Ile Leu Ala Leu Ile Ala Phe Ile Cys Ile Glu Thr
1               5                   10                  15

Ile Met Ala

<210> SEQ ID NO 22
<211> LENGTH: 29
<212> TYPE: PRT
<213> ORGANISM: Artificial Sequence
<220> FEATURE:
<223> OTHER INFORMATION: synthetic peptide

<400> SEQUENCE: 22

Gly Leu Tyr Phe Phe Glu Phe Val Ser Cys Ser Ala Phe Val Val Thr
1               5                   10                  15

Gly Val Leu Leu Ile Met Phe Ser Leu Asn Leu His Met
            20                  25

<210> SEQ ID NO 23
<211> LENGTH: 23
<212> TYPE: PRT
<213> ORGANISM: Artificial Sequence
<220> FEATURE:
<223> OTHER INFORMATION: synthetic peptide

<400> SEQUENCE: 23

Leu Val Asn Thr Gly Leu Ser Thr Phe Leu Phe Phe Ile Ala Ser Ile
1               5                   10                  15

Val Leu Ala Thr Leu Asn His
```

```
<210> SEQ ID NO 24
<211> LENGTH: 22
<212> TYPE: PRT
<213> ORGANISM: Artificial Sequence
<220> FEATURE:
<223> OTHER INFORMATION: synthetic peptide

<400> SEQUENCE: 24

Ile Ala Ala Val Ile Phe Gly Phe Leu Ala Thr Ala Ala Tyr Ala Val
1               5                   10                  15

Asn Thr Phe Leu Ala Val
            20

<210> SEQ ID NO 25
<211> LENGTH: 14
<212> TYPE: PRT
<213> ORGANISM: Artificial Sequence
<220> FEATURE:
<223> OTHER INFORMATION: synthetic peptide

<400> SEQUENCE: 25

Arg Ser Arg Lys Tyr Thr Ser Trp Tyr Val Ala Leu Lys Arg
1               5                   10

<210> SEQ ID NO 26
<211> LENGTH: 19
<212> TYPE: PRT
<213> ORGANISM: Artificial Sequence
<220> FEATURE:
<223> OTHER INFORMATION: synthetic peptide

<400> SEQUENCE: 26

Met Ala Lys Ser Ile Arg Ser Lys His Arg Arg Gln Met Arg Met Met
1               5                   10                  15

Lys Arg Glu

<210> SEQ ID NO 27
<211> LENGTH: 16
<212> TYPE: PRT
<213> ORGANISM: Artificial Sequence
<220> FEATURE:
<223> OTHER INFORMATION: synthetic peptide

<400> SEQUENCE: 27

Met Ala Arg Arg Arg Arg His Arg Gly Pro Arg Arg Pro Arg Pro Pro
1               5                   10                  15

<210> SEQ ID NO 28
<211> LENGTH: 19
<212> TYPE: PRT
<213> ORGANISM: Artificial Sequence
<220> FEATURE:
<223> OTHER INFORMATION: synthetic peptide

<400> SEQUENCE: 28

Gly Arg Cys Arg Arg Leu Ala Asn Phe Gly Pro Arg Lys Arg Arg Arg
1               5                   10                  15

Arg Arg Arg

<210> SEQ ID NO 29
<211> LENGTH: 16
<212> TYPE: PRT
<213> ORGANISM: Artificial Sequence
```

```
<220> FEATURE:
<223> OTHER INFORMATION: synthetic peptide

<400> SEQUENCE: 29

Arg Arg Arg Lys Arg Asn Arg Asp Ala Arg Arg Arg Arg Lys Gln
1               5                   10                  15

<210> SEQ ID NO 30
<211> LENGTH: 17
<212> TYPE: PRT
<213> ORGANISM: Artificial Sequence
<220> FEATURE:
<223> OTHER INFORMATION: synthetic peptide

<400> SEQUENCE: 30

Met Gln Arg Lys Pro Thr Ile Arg Arg Lys Asn Leu Arg Leu Arg Arg
1               5                   10                  15

Lys

<210> SEQ ID NO 31
<211> LENGTH: 7
<212> TYPE: PRT
<213> ORGANISM: Artificial Sequence
<220> FEATURE:
<223> OTHER INFORMATION: synthetic peptide

<400> SEQUENCE: 31

Ile Met Arg Arg Arg Gly Leu
1               5

<210> SEQ ID NO 32
<211> LENGTH: 8
<212> TYPE: PRT
<213> ORGANISM: Artificial Sequence
<220> FEATURE:
<223> OTHER INFORMATION: synthetic peptide

<400> SEQUENCE: 32

Lys Lys Leu Lys Lys Arg Asn Lys
1               5

<210> SEQ ID NO 33
<211> LENGTH: 9
<212> TYPE: PRT
<213> ORGANISM: Artificial Sequence
<220> FEATURE:
<223> OTHER INFORMATION: synthetic peptide

<400> SEQUENCE: 33

Arg Arg Arg Ala Asn Asn Arg Arg Arg
1               5

<210> SEQ ID NO 34
<211> LENGTH: 7
<212> TYPE: PRT
<213> ORGANISM: Artificial Sequence
<220> FEATURE:
<223> OTHER INFORMATION: synthetic peptide

<400> SEQUENCE: 34

Arg Lys Lys Arg Lys Lys Lys
1               5

<210> SEQ ID NO 35
<211> LENGTH: 15
<212> TYPE: PRT
```

```
<213> ORGANISM: Artificial Sequence
<220> FEATURE:
<223> OTHER INFORMATION: synthetic peptide

<400> SEQUENCE: 35

Lys Arg Lys Gly Lys Leu Lys Asn Lys Gly Ser Lys Arg Lys Lys
1               5                   10                  15

<210> SEQ ID NO 36
<211> LENGTH: 18
<212> TYPE: PRT
<213> ORGANISM: Artificial Sequence
<220> FEATURE:
<223> OTHER INFORMATION: synthetic peptide

<400> SEQUENCE: 36

Ser Lys Arg Leu Ser Ser Arg Ala Arg Lys Arg Ala Ala Lys Arg Arg
1               5                   10                  15

Leu Gly

<210> SEQ ID NO 37
<211> LENGTH: 14
<212> TYPE: PRT
<213> ORGANISM: Artificial Sequence
<220> FEATURE:
<223> OTHER INFORMATION: synthetic peptide

<400> SEQUENCE: 37

Lys Arg Pro Arg Arg Arg Pro Ser Arg Pro Phe Arg Lys Pro
1               5                   10

<210> SEQ ID NO 38
<211> LENGTH: 13
<212> TYPE: PRT
<213> ORGANISM: Artificial Sequence
<220> FEATURE:
<223> OTHER INFORMATION: synthetic peptide

<400> SEQUENCE: 38

Lys Lys Arg Thr Leu Arg Lys Asn Asp Arg Lys Lys Arg
1               5                   10

<210> SEQ ID NO 39
<211> LENGTH: 8
<212> TYPE: PRT
<213> ORGANISM: Artificial Sequence
<220> FEATURE:
<223> OTHER INFORMATION: synthetic peptide

<400> SEQUENCE: 39

Trp Arg Arg Gln Ala Arg Phe Lys
1               5

<210> SEQ ID NO 40
<211> LENGTH: 9
<212> TYPE: PRT
<213> ORGANISM: Artificial Sequence
<220> FEATURE:
<223> OTHER INFORMATION: synthetic peptide

<400> SEQUENCE: 40

Arg Lys Lys Arg Arg Gln Arg Arg Arg
1               5

<210> SEQ ID NO 41
<211> LENGTH: 11
```

```
<212> TYPE: PRT
<213> ORGANISM: Artificial Sequence
<220> FEATURE:
<223> OTHER INFORMATION: synthetic peptide

<400> SEQUENCE: 41

Tyr Ala Arg Ala Ala Ala Arg Gln Ala Arg Ala
1               5                   10

<210> SEQ ID NO 42
<211> LENGTH: 18
<212> TYPE: PRT
<213> ORGANISM: Artificial Sequence
<220> FEATURE:
<223> OTHER INFORMATION: synthetic peptide

<400> SEQUENCE: 42

Lys Gly Arg Gln Val Lys Val Trp Phe Gln Asn Arg Arg Met Lys Trp
1               5                   10                  15

Lys Lys

<210> SEQ ID NO 43
<211> LENGTH: 34
<212> TYPE: PRT
<213> ORGANISM: Artificial Sequence
<220> FEATURE:
<223> OTHER INFORMATION: synthetic peptide

<400> SEQUENCE: 43

Val Ala Gln Val Ile Leu Ala Leu Ile Ala Phe Ile Cys Ile Glu Thr
1               5                   10                  15

Ile Met Ala Cys Ser Lys Lys Arg Thr Leu Arg Lys Asn Asp Arg Lys
            20                  25                  30

Lys Arg

<210> SEQ ID NO 44
<211> LENGTH: 34
<212> TYPE: PRT
<213> ORGANISM: Artificial Sequence
<220> FEATURE:
<223> OTHER INFORMATION: synthetic peptide

<400> SEQUENCE: 44

Tyr Phe Phe Glu Phe Val Ser Cys Ser Ala Phe Val Val Thr Gly Val
1               5                   10                  15

Leu Leu Ile Met Phe Lys Lys Arg Thr Leu Arg Lys Asn Asp Arg Lys
            20                  25                  30

Lys Arg

<210> SEQ ID NO 45
<211> LENGTH: 34
<212> TYPE: PRT
<213> ORGANISM: Artificial Sequence
<220> FEATURE:
<223> OTHER INFORMATION: synthetic peptide

<400> SEQUENCE: 45

Leu Val Asn Thr Gly Leu Ser Ala Phe Leu Phe Phe Ile Ala Ser Ile
1               5                   10                  15

Val Leu Ala Ala Leu Lys Lys Arg Thr Leu Arg Lys Asn Asp Arg Lys
            20                  25                  30

Lys Arg
```

```
<210> SEQ ID NO 46
<211> LENGTH: 34
<212> TYPE: PRT
<213> ORGANISM: Artificial Sequence
<220> FEATURE:
<223> OTHER INFORMATION: synthetic peptide

<400> SEQUENCE: 46

Ile Ala Ala Val Ile Phe Gly Phe Leu Ala Thr Ala Ala Tyr Ala Val
1               5                   10                  15

Asn Thr Phe Leu Ala Lys Lys Arg Thr Leu Arg Lys Asn Asp Arg Lys
            20                  25                  30

Lys Arg

<210> SEQ ID NO 47
<211> LENGTH: 38
<212> TYPE: PRT
<213> ORGANISM: Artificial Sequence
<220> FEATURE:
<223> OTHER INFORMATION: synthetic peptide

<400> SEQUENCE: 47

Met Gly Ser Asn Leu Ser Pro Gln Leu Cys Leu Met Pro Phe Ile Leu
1               5                   10                  15

Gly Leu Leu Ser Gly Gly Val Thr Thr Lys Lys Arg Thr Leu Arg Lys
            20                  25                  30

Asn Asp Arg Lys Lys Arg
            35
```

ANTITUMOR PEPTIDE AND USE THEREOF

CROSS-REFERENCE TO RELATED APPLICATIONS

Priority is claimed on Japanese Patent Application No. 2019-116906, filed Jun. 25, 2019, the content of which is incorporated herein by reference.

TECHNICAL FIELD

The present invention relates to an artificially synthesized antitumor peptide that can inhibit proliferation of tumor cells and use thereof, and specifically, to use of a synthetic peptide including an amino acid sequence constituting a transmembrane region of chemokine-like factor (CLFK)-like MARVEL transmembrane domain containing family member 4 (CMTM4) and a membrane permeable peptide sequence.

TECHNICAL BACKGROUND

Examples of main cancer treatment methods include so-called "three main treatments" such as surgery, radiation therapy, and chemotherapy. In recent years, in addition to them, research has been actively conducted to develop "immunotherapy" against cancer using the functions of the immune system.

Cancerous cells (cancer cells, tumor cells) are recognized as foreign substances in a living body and can be eliminated by an immune monitoring mechanism. However, various research has clearly found that tumor cells express certain molecules (for example, proteins and lipids), and avoid attack by an immune monitoring mechanism. Specifically, for example, "programmed cell death-1 ligand-1 (PD-L1: also referred to as B7-H1)" may be expressed on the surface of tumor cells. It is known that tumor cells that express PD-L1 can inhibit functions of immune cells (for example, T cells) that express PD-1 which is a receptor of PD-L1. For example, when an interaction between PD-1 and PD-L1 is blocked, inhibition of immune cells by PD-L1 is prevented. Therefore, immune cells can attack tumor cells. Thus, it is confirmed in Patent Document 1 (WO 2004/004771) that proliferation of some tumors is inhibited by administering anti-PD-L1 antibodies. In addition, the effect of anti-PD-L1 antibodies has been clinically recognized.

On the other hand, research on tumor microenvironments has been actively performed. Specifically, molecules that interact with PD-L1 in tumor cells (including the inside of tumor details and cell membranes) have been studied, for example, as in Non-Patent Document 1 (Identification of CMTM6 and CMTM4 as PD-L1 protein regulators. Mezzadra, et. al., 2017, Nature, 549, 106-110) and Non-Patent Document 2 (Novel regulators of PD-L1 expression in cancer: CMTM6 and CMTM4-a new avenue to enhance the therapeutic benefits of immune checkpoint inhibitors. Imamovic and Vranic, 2017, Annals of Translational Medicine, 5, 467). Thus, this non-patent document shows that expression of PD-L1 on the surface of tumor cells can be promoted by, for example, CMTM4 and CMTM6 membrane proteins.

Incidentally, when anti-PD-L1 antibodies are used, for example, a certain treatment effect may be obtained even if cancer becomes unresectable due to metastasis. However, the cost of a cancer treatment becomes a serious problem due to use of drugs containing expensive antibodies as a main component.

Thus, an object of the present invention is to provide a synthetic peptide having a configuration different from that of an antitumor agent using expensive antibodies and having antitumor (anticancer) performance.

SUMMARY OF THE INVENTION

The inventors have focused on a transmembrane region of a membrane protein chemokine-like factor (CLFK)-like MARVEL transmembrane domain containing family member 4 (CMTM4) expressed in species, and particularly, mammals. Thus, the inventors surprisingly found that a synthetic peptide in which four amino acid sequences constituting the transmembrane region of CMTM4 and an amino acid sequence constituting a conventional known cell membrane permeable peptide (CPP) are combined has excellent antitumor properties (anti-cancer properties) with respect to various tumor cells, and thereby the present invention was completed.

Specifically, the synthetic peptide disclosed here is a synthetic peptide that inhibits proliferation of at least one species of tumor cells, the synthetic peptide including the following amino acid sequences (1) and (2):

(1) a CMTM4-TM-related sequence which is an amino acid sequence constituting a transmembrane region of CMTM4 (chemokine-like factor (CLFK)-like MARVEL transmembrane domain containing family member 4) which is a membrane protein, the CMTM4-TM-related sequence being any one of the following i) to iv):

i) an amino acid sequence constituting the first transmembrane region from an N-terminal of CMTM4, or
a modified amino acid sequence in which 1, 2, or 3 amino acid residues are deleted, substituted or added in the amino acid sequence;

ii) an amino acid sequence constituting the second transmembrane region from the N-terminal of CMTM4, or
a modified amino acid sequence in which 1, 2, or 3 amino acid residues are deleted, substituted or added in the amino acid sequence;

iii) an amino acid sequence constituting the third transmembrane region from the N-terminal of CMTM4, or
a modified amino acid sequence in which 1, 2, or 3 amino acid residues are deleted, substituted or added in the amino acid sequence;

iv) an amino acid sequence constituting the fourth transmembrane region from the N-terminal of CMTM4, or
a modified amino acid sequence in which 1, 2, or 3 amino acid residues are deleted, substituted or added in the amino acid sequence; and (2) a CPP-related sequence which is an amino acid sequence that functions as a membrane permeable peptide.

In a preferable aspect, the synthetic peptide disclosed here has a total number of amino acid residues of 100 or less. In consideration of production costs, ease of synthesis, and handling properties, more preferably, the total number of amino acid residues is 80 or less (for example, 70 or less).

Alternatively, a synthetic peptide in which a combined proportion of the amino acid sequence shown in (1) and the amino acid sequence shown in (2), expressed as a percentage of the number of amino acids, is 80% or more (more preferably 90% or more, for example, 100%) of the total thereof is a particularly suitable aspect among the synthetic peptides disclosed here.

In a preferable aspect, the CMTM4-TM-related sequence includes an amino acid sequence shown in any of SEQ ID Nos: 1 to 4.

In addition, in another preferable aspect of the synthetic peptide disclosed here, the CPP-related sequence is a polyarginine (although not particularly limited, typically, composed of 5 or more and 9 or less arginine residues), or an amino acid sequence shown in any of SEQ ID Nos: 25 to 42, or a modified amino acid sequence in which 1, 2, or 3 amino acid residues are deleted, substituted or added in the amino acid sequence.

For example, a synthetic peptide including:

(i) an amino acid sequence shown in any of SEQ ID Nos: 1 to 4, or a modified amino acid sequence in which one or more (for example, 2 or 3) amino acid residues are deleted, substituted or added in the amino acid sequence; and (ii) a polyarginine, or an amino acid sequence shown in any of SEQ ID Nos: 25 to 42 or a modified amino acid sequence in which 1, 2, or 3 amino acid residues are deleted, substituted or added in the amino acid sequence, may be exemplified as a preferable example.

In another preferable aspect of the synthetic peptide disclosed here, the CPP-related sequence is adjacent to the N-terminal or C-terminal side of the CMTM4-TM-related sequence. Alternatively, the CPP-related sequence is arranged via a linker composed of 10 or less (preferably 5 or less, for example, 1 or 2) amino acid residues.

In a preferable aspect, the synthetic peptide disclosed here includes an amino acid sequence shown in any of SEQ ID Nos: 43 to 46.

In addition, the present invention provides an antitumor composition that inhibits proliferation of at least one species of tumor cells, the antitumor composition including any of the synthetic peptides (antitumor peptides) disclosed here and at least one pharmaceutically acceptable carrier.

Such a composition that contains the synthetic peptide disclosed here can be used as an antitumor agent (including an anti-cancer agent; the same applies hereinafter) or a material for development of a novel antitumor agent.

In addition, the present invention provides a method of inhibiting proliferation of at least one species of tumor cells, the method including supplying any of the synthetic peptides (antitumor peptides) disclosed here to target tumor cells (for example, outside a living organism, i.e. in vitro or inside a living organism, i.e. in vivo) at least once.

In the method in such a configuration, when the synthetic peptide disclosed here is supplied to tumor cells, it is possible to prevent or inhibit proliferation of the tumor cells (preferably, further enlargement in tumor or cancer tissues).

DESCRIPTION OF THE RELATED EMBODIMENTS

Preferable embodiments of the present invention will be described below. Components other than those particularly mentioned in this specification (for example, the primary structure and chain length of the synthetic peptide disclosed here) that are necessary for implementation of the present invention (for example, a method of chemically synthesizing a peptide, a cell culture technique, and a general method of preparing a pharmaceutical composition including a peptide as a component) can be recognized by those skilled in the art as design matters based on the related art in the fields of cell engineering, physiology, medicine, pharmacy, organic chemistry, biochemistry, genetic engineering, protein engineering, molecular biology, genetics, and the like. The present invention can be implemented based on content disclosed in this specification and common general technical knowledge in the field. Here, in the following description, amino acids are represented by one-letter symbols (but, three-letter symbols in the sequence listing).

The entire content of all documents cited in this specification is incorporated herein by reference.

In this specification, "tumor" is a term that is interpreted in a broad sense, and refers to a general tumor (typically, a malignant tumor) including a carcinoma and sarcoma or blood or hematopoietic tissue lesions (leukemia, lymphoma, etc.). In addition, "tumor cell" is the same as "cancer cell", and refers to cells that form such a tumor and cells (so-called cancerous cells) that typically abnormally proliferate regardless of surrounding normal tissues. Therefore, unless otherwise specified, cells that are classified as tumor cells (cancer cells) rather than normal cells are referred to as tumor cells regardless of the origin or properties of the cells. Cells constituting epithelial tumors (squamous cell carcinoma, adenocarcinoma, etc.), non-epithelial tumors (various sarcomas and osteosarcomas, etc.), various cell tumors (neuroblastoma, retinoblastoma, etc.), lymphoma, melanoma, or the like are typical examples included in the tumor cells mentioned here.

In addition, "synthetic peptide" in this specification refers to a peptide fragment of which a peptide chain alone is not independently and stably present in nature, but is produced through artificial chemical synthesis or biosynthesis (that is, production based on genetic engineering) and can be stably present in a predetermined composition. Here, the term "peptide" refers to an amino acid polymer having a plurality of peptide bonds, and although the number of amino acid residues included in the peptide chain is not limited, the peptide is a relatively low molecular-weight polymer, typically, a total number of amino acid residues being about 100 or less (preferably 80 or less, more preferably 70 or less, and particularly preferably 50 or less).

In addition, the term "amino acid residue" in this specification includes an N-terminal amino acid and a C-terminal amino acid of a peptide chain unless otherwise specified.

Here, always, the left side of the amino acid sequences described in this specification is the N-terminal side, and the right side thereof is the C-terminal side.

The "modified amino acid sequence" with respect to a predetermined amino acid sequence in this specification refers to an amino acid sequence formed when one to several (typically, 9 or less, and preferably 5 or less) amino acid residues, for example, 1, 2, or 3 amino acid residues are substituted, deleted or added (inserted) without impairing functions (for example, antitumor activity and cell membrane permeability) of the predetermined amino acid sequence. For example, a sequence generated by so-called conservative substitution (conservative amino acid substitution) in which 1, 2, or 3 amino acid residues are conservatively substituted (for example, a sequence in which a basic amino acid residue is substituted with another basic amino acid residue: for example, a lysine residue and an arginine residue are substituted with each other), a sequence in which 1, 2, or 3 amino acid residues are added (inserted) to or deleted from a predetermined amino acid sequence, and the like are typical examples included in the modified amino acid sequence referred to in this specification. Accordingly, the synthetic peptide disclosed as an example here includes, in addition to a synthetic peptide composed of the same amino acid sequences as the amino acid sequences of SEQ ID Nos, synthetic peptides composed of modified amino acid sequences in which 1, 2, or 3 amino acid residues are substituted (for example, the above conservative substitution), deleted or added in amino acid sequences of SEQ ID Nos which are amino acid sequences exhibiting the same antitumor activity.

The synthetic peptide that is artificially synthesized disclosed here is a short chain peptide that does not occur in nature and that the inventors found to inhibit proliferation of tumor cells (that is, antitumor activity), and is a peptide including the above two amino acid sequences, that is, (1) a CMTM4-TM-related sequence, and
(2) a CPP-related sequence.

Here, the CMTM4-TM-related sequence refers to an amino acid sequence which constitutes a transmembrane region of proteins constituting CMTM4 (chemokine-like factor (CLFK)-like MARVEL transmembrane domain containing family member 4) or its modified amino acid sequence and has antitumor activity.

CMTM4 is a membrane protein composed of typically about 234 amino acid residues and has four transmembrane regions (UniProtKB-Q8IZR5). Non-Patent Document 1 and Non-Patent Document 2 listed above show that CMTM4 has a function of promoting expression of PD-L1 in tumor cells.

However, it has not been found that the transmembrane region of CMTM4 itself has antitumor activity, and the fact that an artificially synthesized antitumor peptide is obtained synthesizing an amino acid sequence of such a peptide region and adding a CPP to the sequence was not completely unexpected at the time of filing this application.

For example, information on genes (including the case of cDNA) encoding CMTM4 and amino acid sequence information can be obtained by accessing knowledge bases (databases) in various public international organizations. For example, all amino acid sequence information of CMTM4 derived from various species and amino acid sequence information of the transmembrane region can be obtained in Universal Protein Resource (UniProt). According to the database, at least information on CMTM4 in mammals such as humans, mice, rats, chimpanzees, hamsters, and monkeys can be obtained.

The CMTM4-TM-related sequences according to the above (1) preferably used for implementing the present invention are shown in, for example, SEQ ID Nos: 1 to 4.

Specifically, the amino acid sequence of SEQ ID No: 1 is an amino acid sequence composed of a total of 21 amino acid residues constituting the first transmembrane region from the N-terminal from human-derived CMTM4.

In addition, the amino acid sequence of SEQ ID No: 2 is an amino acid sequence composed of a total of 21 amino acid residues constituting the second transmembrane region from the N-terminal of human-derived CMTM4.

In addition, the amino acid sequence of SEQ ID No: 3 is an amino acid sequence composed of a total of 21 amino acid residues constituting the third transmembrane region from the N-terminal of human-derived CMTM4.

In addition, the amino acid sequence of SEQ ID No: 4 is an amino acid sequence composed of a total of 21 amino acid residues constituting the fourth transmembrane region from the N-terminal of human-derived CMTM4.

Here, in the SEQ ID Nos: 1 to 4, TM sequences of human-derived CMTM4 are shown, but the sequences are only examples, and available amino acid sequences are not limited thereto.

For example, the amino acid sequence of SEQ ID No: 5 is an amino acid sequence composed of a total of 21 amino acid residues constituting the first transmembrane region from the N-terminal of mouse-derived CMTM4 (UniProtKB-Q8CJ61).

In addition, the amino acid sequence of SEQ ID No: 6 is an amino acid sequence composed of a total of 21 amino acid residues constituting the second transmembrane region from the N-terminal of mouse-derived CMTM4.

In addition, the amino acid sequence of SEQ ID No: 7 is an amino acid sequence composed of a total of 21 amino acid residues constituting the third transmembrane region from the N-terminal of mouse-derived CMTM4.

In addition, the amino acid sequence of SEQ ID No: 8 is an amino acid sequence composed of a total of 21 amino acid residues constituting the fourth transmembrane region from the N-terminal of mouse-derived CMTM4.

In addition, the amino acid sequence of SEQ ID No: 9 is an amino acid sequence composed of a total of 18 amino acid residues constituting the first transmembrane region from the N-terminal of rat-derived CMTM4 (UniProtKBD4A110).

In addition, the amino acid sequence of SEQ ID No: 10 is an amino acid sequence composed of a total of 24 amino acid residues constituting the second transmembrane region from the N-terminal of rat-derived CMTM4.

In addition, the amino acid sequence of SEQ ID No: 11 is an amino acid sequence composed of a total of 23 amino acid residues constituting the third transmembrane region from the N-terminal of rat-derived CMTM4.

In addition, the amino acid sequence of SEQ ID No: 12 is an amino acid sequence composed of a total of 22 amino acid residues constituting the fourth transmembrane region from the N-terminal of rat-derived CMTM4.

In addition, the amino acid sequence of SEQ ID No: 13 is an amino acid sequence composed of a total of 19 amino acid residues constituting the first transmembrane region from the N-terminal of chimpanzee-derived CMTM4 (UniProtKB-A0A2R9AGF5).

In addition, the amino acid sequence of SEQ ID No: 14 is an amino acid sequence composed of a total of 29 amino acid residues constituting the second transmembrane region from the N-terminal of chimpanzee-derived CMTM4.

In addition, the amino acid sequence of SEQ ID No: 15 is an amino acid sequence composed of a total of 23 amino acid residues constituting the third transmembrane region the N-terminal of chimpanzee-derived CMTM4.

In addition, the amino acid sequence of SEQ ID No: 16 is an amino acid sequence composed of a total of 22 amino acid residues constituting the fourth transmembrane region from the N-terminal of chimpanzee-derived CMTM4.

In addition, the amino acid sequence of SEQ ID No: 17 is an amino acid sequence composed of a total of 18 amino acid residues constituting the first transmembrane region from the N-terminal of hamster-derived CMTM4 (UniProtKB-A0A1U7R0V6).

In addition, the amino acid sequence of SEQ ID No 18: is an amino acid sequence composed of a total of 24 amino acid residues constituting the second transmembrane region from the N-terminal of hamster-derived CMTM4.

In addition, the amino acid sequence of SEQ ID No: 19 is an amino acid sequence composed of a total of 23 amino acid residues constituting the third transmembrane region from the N-terminal of hamster-derived CMTM4.

In addition, the amino acid sequence of SEQ ID No: 20 is an amino acid sequence composed of a total of 22 amino acid residues constituting the fourth transmembrane region from the N-terminal of hamster-derived CMTM4.

In addition, the amino acid sequence of SEQ ID No: 21 is an amino acid sequence composed of a total of 19 amino acid residues constituting the first transmembrane region from the N-terminal of green monkey-derived CMTM4 (UniProtKB-A0A0D9QX78).

In addition, the amino acid sequence of SEQ ID No: 22 is an amino acid sequence composed of a total of 29 amino acid residues constituting the second transmembrane region from the N-terminal of green monkey-derived CMTM4.

In addition, the amino acid sequence of SEQ ID No: 23 is an amino acid sequence composed of a total of 23 amino acid residues constituting the third transmembrane region from the N-terminal of green monkey-derived CMTM4.

In addition, the amino acid sequence of SEQ ID No: 24 is an amino acid sequence composed of a total of 22 amino acid residues constituting the fourth transmembrane region from the N-terminal of green monkey-derived CMTM4.

Any of the amino acid sequences shown in the above SEQ ID Nos: 1 to 24 can be used for an antitumor peptide.

When the present invention is implemented, in order to exhibit a stronger antitumor effect, an amino acid sequence constituting the third or fourth transmembrane region from the N-terminal of CMTM4 or its modified amino acid sequence is preferably used as the CMTM4-TM-related sequence. In addition, an amino acid sequence constituting the third transmembrane region from the N-terminal of CMTM4 or its modified amino acid sequence is more preferably used.

Regarding an amino acid sequence that functions as a CPP (that is, a CPP-related sequence) that is used to construct a synthetic peptide disclosed here, various conventionally known CPPs can be used. For example, a so-called polyarginine (Rn) composed of 3 or more, preferably 5 or more, 11 or less, and preferably 9 or less arginine residues, is suitable as a CPP used here. In addition, various known CPPs can be used.

Although not particularly limited, SEQ ID Nos: 25 to 42 are preferable examples of an amino acid sequence that functions as a CPP. Specifically, the SEQ ID Nos are as follows.

The amino acid sequence of SEQ ID No: 25 corresponds to nucleolar localization signal (NoLS) composed of a total of 14 amino acid residues derived from basic fibroblast growth factor (FGF2).

The amino acid sequence of SEQ ID No: 26 corresponds to NoLS composed of a total of 19 amino acid residues derived from one species (ApLLP) of nucleolar proteins.

The amino acid sequence of SEQ ID No: 27 corresponds to NoLS composed of a total of 16 amino acid residues derived from a protein (γ(1)34.5) of herpes simplex virus type 1 (HSV-1).

The amino acid sequence of SEQ ID No: 28 corresponds to NoLS composed of a total of 19 amino acid residues derived from a p40 protein of human I-mfa domain-containing protein (HIC).

The amino acid sequence of SEQ ID No: 29 corresponds to NoLS composed of a total of 16 amino acid residues derived from an MEQ protein of Marek disease virus (MDV).

The amino acid sequence of SEQ ID No: 30 corresponds to NoLS composed of a total of 17 amino acid residues derived from SurvivindeltaEx3 which is a protein that inhibits apoptosis.

The amino acid sequence of SEQ ID No: 31 corresponds to NoLS composed of a total of 7 amino acid residues derived from Angiogenin which is a vascular growth factor.

The amino acid sequence of SEQ ID No: 32 corresponds to NoLS composed of a total of 8 amino acid residues derived from MDM2 which is a nuclear phosphoprotein and forms a complex with p53 tumor inhibiting protein.

The amino acid sequence of SEQ ID No: 33 corresponds to NoLS composed of a total of 9 amino acid residues derived from GGNNVα which is a betanoda virus protein.

The amino acid sequence of SEQ ID No: 34 corresponds to NoLS composed of a total of 7 amino acid residues derived from NF-κB inducible kinase (NIK).

The amino acid sequence of SEQ ID No: 35 corresponds to NoLS composed of a total of 15 amino acid residues derived from a nuclear VCP-like protein.

The amino acid sequence of SEQ ID No: 36 corresponds to NoLS composed of a total of 18 amino acid residues derived from p120 which is a nucleolar protein.

The amino acid sequence of SEQ ID No: 37 corresponds to NoLS composed of a total of 14 amino acid residues derived from an ORF57 protein of herpes virus saimiri (HVS).

The amino acid sequence of SEQ ID No: 38 corresponds to NoLS composed of a total of 13 amino acid residues from the 491st amino acid residue to the 503rd amino acid residue of LIM kinase 2 present in human endothelial cells, which is one of protein kinases related to intracellular signal transduction.

The amino acid sequence of SEQ ID No: 39 corresponds to NoLS composed of a total of 8 amino acid residues included in the nucleocapsid protein (N protein) of avian infectious bronchitis virus (IBV).

The amino acid sequence of SEQ ID No: 40 corresponds to a membrane-permeable motif composed of a total of 9 amino acid sequences derived from the protein transduction domain included in TAT of human immunodeficiency virus (HIV).

The amino acid sequence of SEQ ID No: 41 corresponds to a membrane-permeable motif composed of a total of 11 amino acid sequences of the protein transduction domain (PTD4) obtained by modifying the above TAT.

The amino acid sequence of SEQ ID No: 42 corresponds to a membrane-permeable motif composed of a total of 18 amino acid sequences derived from ANT of Antennapedia which is a variant of *Drosophila*.

Among these, particularly, amino acid sequences related to NoLS and TAT (or modified amino acid sequences thereof) are preferable. For example, the CPP sequence related to NoLS as shown in SEQ ID No: 38 and SEQ ID No: 39 or the CPP sequences related to TAT and ANT as shown in SEQ ID Nos: 40 to 42 can be suitably used to construct the synthetic peptide disclosed here.

Here, modified amino acid sequences that function as a CPP in which 1, 2, or 3 amino acid residues are deleted, substituted or added in the sequences of SEQ ID Nos: 25 to 42 can be suitably used to construct the synthetic peptide disclosed here.

A peptide chain (amino acid sequence) of the synthetic peptide disclosed here may include the
(1) CMTM4-TM-related sequence, and
(2) CPP-related sequence
as described above, and for example, the CPP-related sequence may be relatively arranged on the N-terminal side or C-terminal side of the CMTM4-TM-related sequence.

In addition, preferably, the CMTM4-TM-related sequence and the CPP-related sequence are arranged adjacent to each other.

Specifically, there are preferably no amino acid residues that are not included in both sequence parts between the CMTM4-TM-related sequence and the CPP-related sequence. Alternatively, even if there are linkers, the number of linkers connecting the above two sequences is preferably 10 or less (more preferably 5 or less, for example, 1 or 2 amino acid residues).

As long as the antitumor activity with which proliferation of at least one species of tumor cells can be inhibited is not impaired, a sequence (amino acid residue) part other than the amino acid sequence constituting the CMTM4-TM-related sequence and the CPP-related sequence can be contained.

In the synthetic peptide disclosed here, a total number of amino acid residues constituting the peptide chain is suitably 100 or less, preferably 80 or less, and preferably 70 or less (for example, a peptide chain of about 25 to 45). Such a peptide with a short chain length is easily chemically synthesized and a synthetic peptide can be easily provided. Although not particularly limited, a linear or helical form is preferable because it is less likely to become an immunogen (antigen). A peptide in such a form is less likely to constitute an epitope.

A proportion of the CMTM4-TM-related sequence and the CPP-related sequence with respect to the total number of amino acid sequences of the synthesized peptide is not particularly limited as long as the antitumor activity is not impaired, but the proportion is, expressed as a percentage of the number of amino acids, desirably about 80% or more and preferably 90% or more. Here, it is preferable that all amino acid residues be L-type amino acids. However, some or all of amino acid residues may be substituted with D-type amino acids as long as the antitumor activity is not impaired.

Preferably, in the synthetic peptide disclosed here, at least one amino acid residue is preferably amidated. When a carboxyl group of an amino acid residue (typically, a C-terminal amino acid residue of the peptide chain) is amidated, it is possible to improve structural stability (for example, protease resistance) of the synthetic peptide. For example, when a CPP-related sequence part constitutes a C-terminal of the synthetic peptide, the C-terminal amino acid residue of the sequence part is preferably amidated. On the other hand, when a CMTM4-TM-related sequence part constitutes a C-terminal of the synthetic peptide, the C-terminal amino acid residue of the sequence part is preferably amidated. In another preferable aspect, for example, the stability of the synthetic peptide can be improved by amidating the C-terminal amino acid residue of the synthetic peptide having amino acid sequences of SEQ ID Nos: 43 to 46.

The synthetic peptide disclosed here can be easily produced according to a general chemical synthesis method. For example, any of conventionally known solid-phase synthesis methods and liquid phase synthesis methods may be used. A solid-phase synthesis method in which t-butyloxycarbonyl (Boc) or 9-fluorenylmethoxycarbonyl (Fmoc) is applied as a protecting group for an amino group is suitable.

Regarding the synthetic peptide disclosed here, a peptide chain having a desired amino acid sequence and a modified (C-terminal amidation, etc.) part can be synthesized according to a solid-phase synthesis method using a commercially available peptide synthesizer.

Alternatively, a synthetic peptide may be produced through biosynthesis based on a genetic engineering technique. That is, a polynucleotide (typically, DNA) of a nucleotide sequence (including an ATG start codon) that encodes an amino acid sequence of a desired synthetic peptide is synthesized. Then, a recombinant vector having a genetic construct for expression composed of the synthesized polynucleotide (DNA) and various regulatory elements (including promoters, ribosome binding sites, terminators, enhancers, and various cis elements that controls an expression level) for expressing the amino acid sequence in host cells is constructed according to host cells.

According to a general technique, the recombinant vector is introduced into predetermined host cells (for example yeast, insect cells, and plant cells), and the host cells or tissues or subjects containing the cells are cultured under predetermined conditions. Accordingly, desired peptides can be expressed and produced in cells. Then, peptides are isolated from host cells (in a culture medium if secreted), and as necessary, refolding, purification, and the like are performed, and thereby a desired synthetic peptide can be obtained.

Here, regarding a method of constructing a recombinant vector, a method of introducing a constructed recombinant vector into host cells, and the like, methods conventionally used in the field may be directly used, and such methods themselves do not particularly characterize the present invention, and thus detailed description thereof will be omitted.

Alternatively, a template DNA (that is, a synthetic gene fragment including a nucleotide sequence that encodes an amino acid sequence of a synthetic peptide) for a cell-free protein synthesis system is constructed, various compounds (ATP, RNA polymerase, amino acids, and the like) necessary for peptide synthesis are used, and thus a desired polypeptide can be synthesized in vitro using a so-called cell-free protein synthesis system. Regarding the cell-free protein synthesis system, for example, the paper written by Shimizu et al. (Shimizu et al., Nature Biotechnology, 19, 751-755 (2001)), and the paper written by Madin et al. (Madin et al., Proc. Natl. Acad. Sci. USA, 97(2), 559-564 (2000)) can be referred to. Based on the techniques described in these papers, many companies had already commissioned polypeptides at the time of filing this application, and cell-free protein synthesis kits (for example, commercially available from CellFree Sciences Co., Ltd., Japan) are commercially available.

A single-stranded or double-stranded polynucleotide including a nucleotide sequence that encodes the synthetic peptide disclosed here and/or a nucleotide sequence complementary to the sequence can be easily produced (synthesized) by conventionally known methods. That is, when codons corresponding to amino acid residues constituting a designed amino acid sequence are selected, a nucleotide sequence corresponding to the amino acid sequence of the synthetic peptide is easily determined and provided. Then, once the nucleotide sequence is determined, a (single-stranded) polynucleotide corresponding to a desired nucleotide sequence can be easily obtained using a DNA synthesizer or the like. In addition, desired double-stranded DNA can be obtained using the obtained single-stranded DNA as a template according to various enzymatic synthesis techniques (typically, PCR). In addition, the polynucleotide may be in the form of DNA or in the form of RNA (mRNA, etc.). Double-stranded or single-stranded DNA may be provided. When single-stranded DNA is provided, it may be a coding strand (sense strand) or a non-coding strand (antisense strand) of a sequence complementary thereto.

The polynucleotide obtained in this manner can be used as a material for constructing a recombinant gene (expression cassette) for synthetic peptide production in various host cells or a cell-free protein synthesis system as described above.

The synthetic peptide disclosed here can be suitably used as an effective component of a composition for inhibiting (or suppressing) proliferation of tumor cells (that is, a pharmaceutical antitumor composition such as an antitumor agent). Here, the synthetic peptide may be in a salt form as long as the antitumor activity is not impaired. For example, an acid addition salt of the synthetic peptide that can be obtained by an addition reaction of an inorganic acid or organic acid that is generally used according to a general method can be used. Therefore, "peptide" described in this specification and the claims includes such salt forms.

The antitumor composition disclosed here can contain various pharmaceutically (pharmacologically) acceptable carriers according to the usage form as long as the antitumor activity of the synthetic peptide as an effective component is not impaired. For example, carriers that are generally used in a peptide drug can be applied as a diluent, an excipient, and the like.

The carrier may appropriately vary depending on applications and forms of the antitumor composition disclosed here, but typically, water, a physiological buffer solution, and various organic solvents may be exemplified. The carrier may be a non-drying oil such as an aqueous solution containing an alcohol (such as ethanol) with an appropriate concentration, glycerol, and olive oil. Alternatively, it may be a liposome. In addition, examples of a secondary component that can be contained in the antitumor composition include various fillers, extending agents, binders, moisturizers, surfactants, pigments, and perfumes.

Examples of typical forms of the antitumor composition (antitumor agent) include solutions, suspending agents, emulsions, aerosols, foam agents, granules, powders, tablets, capsules, ointments, and aqueous gels. In addition, for use in injection or the like, lyophilizates and granules for preparing a drug solution by performing dissolving in a saline or a suitable buffer solution (for example, PBS) immediately before use can be provided.

Here, a process itself of preparing various forms of compositions (drugs) including the synthetic peptide (main component) and various carriers (minor component) as materials may be performed according to a conventional known method, and such a production method itself does not characterize the present invention, and thus detailed description thereof will be omitted. Examples of detailed sources of information on formulation include Comprehensive Medicinal Chemistry, edited by Corwin Hansch, Pergamon Press (1990). The entire content in this book is incorporated by reference in this specification.

Cells to which the antitumor composition disclosed here (synthetic peptide) are applied are not particularly limited as long as they are tumor cells (cancer cells), and the antitumor composition can be applied to various species of tumor cells that occur in human or non-human mammals. For example, many kinds of squamous cell carcinoma and adenocarcinoma are included. For example, cancer cells of melanoma, lung cancer (non-small cell lung cancer, small cell lung cancer, alveolar basal epithelial adenocarcinoma, and the like), kidney cancer, and the like or cells of breast cancer, colon cancer, pancreatic cancer, skin cancer such as basal cell carcinoma, neuroblastoma, retinoblastoma, pheochromocytoma, and other cell tumors may be exemplified.

In a cancer treatment, for example, when cancer metastasis is found, patients may not be able to select a surgical treatment. Specifically, for example, a melanoma can be surgically resected when it is in an initial stage. However, since a melanoma is highly metastatic, it may be unresectable when detected. In addition, cases of kidney cancer that are detected in an early stage by abdominal echo and the like have increased, but there are many cases that are detected after cancer is unresectable. The antitumor composition disclosed here (synthetic peptide) can be preferably applied to tumor cells constituting melanoma, kidney cancer, and the like. This can provide more treatment options for a melanoma and kidney cancer.

The antitumor composition disclosed here can be used according to a method and in a dose depending on its form and purpose as in a conventional peptide formulation. For example, only a desired amount of the antitumor composition in the form of a solution can be administered to affected parts (typically, malignant tumor tissues) of patients (that is, a living organism) through intravenous, intramuscular, subcutaneous, intradermal or intraperitoneal injection. Alternatively, a solid form such as a tablet or a gel-like or aqueous jelly-like form such as an ointment can be directly administered to predetermined tissues (that is, an affected part such as tissues and organs including tumor cells). Alternatively, a solid form such as a tablet can be administered orally. In the case of oral administration, in order to prevent digestive enzyme decomposition in the digestive tract, encapsulation or a protective (coating) material is preferably applied.

Alternatively, with respect to tumor cells (including culture cell lines and cell masses, tissues or organs extracted from living bodies) cultured outside a living organism (in vitro), an appropriate amount of the antitumor composition disclosed here (that is, an appropriate amount of the synthetic peptide) may be supplied to a culture medium containing target culture cells (tissue and the like) at least once. The amount supplied each time and the number of times it is supplied are not particularly limited because they can vary depending on conditions such as the species of tumor cells to be cultured, the cell density (cell density when the culture starts), passage number, culture conditions, and culture medium. However, the antitumor composition is preferably added once, twice, or more times so that the concentration of the synthetic peptide in the culture medium is within a range of about 3 μM or more and 100 μM or less, preferably within a range of 5 μM or more and 50 μM or less (for example, 6.25 μM or more and 25 μM or less).

The in vitro antitumor activity evaluation method of the antitumor composition disclosed here is not particularly limited. However, as an example, a method of calculating an antitumor index based on the viability of tumor cells and normal cells may be exemplified.

Specifically, for example, a test using a conventionally known cell proliferation measurement reagent using a tetrazolium salt is performed so that the antitumor index can be calculated. In a preferable aspect, first, the antitumor composition disclosed here is added to a culture solution containing tumor cells, culture is performed for a predetermined time (for example, 24 hours or longer and 72 hours or shorter), and the viability A (%) of tumor cells is calculated. In addition, the viability B (%) of normal cells cultured under the same conditions is calculated. Then, the antitumor index based on the viabilities of tumor cells and normal cells calculated in this manner can be evaluated according to, for example, the following Formula (1):

Antitumor index based on viabilities of tumor cells and normal cells=A/B (1).

That is, when the value obtained in Formula (1) (that is, antitumor index based on viabilities of tumor cells and normal cells) is closer to, for example, 0, the antitumor composition can be evaluated as having selectivity to tumor cells and excellent antitumor activity. Thus, the value is preferably 0.8 or less, more preferably 0.6 or less, and still more preferably 0.3 or less.

For example, the viability A (%) of tumor cells is calculated assuming that the viability of tumor cells cultured using a culture medium (that is, a culture medium containing no synthetic peptide) containing no antitumor composition is set as 100%. In addition, the viability B (%) of normal cells is calculated assuming that the viability of normal cells cultured using a culture medium (that is, a culture medium containing no synthetic peptide) containing no antitumor composition is set as 100%. Alternatively, A (%) and B (%) may be calculated assuming that the viability calculated by performing the same test using a composition containing a synthetic peptide (hereinafter referred to as a "control peptide") having no antitumor activity is set as 100%.

While some examples of the present invention will be described below, the present invention is not intended to be limited to those shown in the examples.

Test Example 1: Synthesis of Peptide

A total of 5 peptides shown in Table 1 were produced using a commercially available peptide synthesizer. Specifically, details are as follows.

Sample 1 was designed as one example and was a synthetic peptide including the amino acid sequence (LIM kinase 2) of SEQ ID No: 38 as the CPP-related sequence on the C-terminal side of the amino acid sequence (SEQ ID No: 1) of the first transmembrane region from the N-terminal of human CMTM4 (SEQ ID No: 43).

Sample 2 was designed as one example and was a synthetic peptide including the amino acid sequence (LIM kinase 2) of SEQ ID No: 38 as the CPP-related sequence on the C-terminal side of the amino acid sequence (SEQ ID No: 2) of the second transmembrane region from the N-terminal of human CMTM4 (SEQ ID No: 44).

Sample 3 was designed as one example and was a synthetic peptide including the amino acid sequence (LIM kinase 2) of SEQ ID No: 38 as the CPP-related sequence on the C-terminal side of the amino acid sequence (SEQ ID No: 2) of the third transmembrane region from the N-terminal of human CMTM4 (SEQ ID No: 45).

Sample 4 was designed as one example and was a synthetic peptide including the amino acid sequence (LIM kinase 2) of SEQ ID No: 38 as the CPP-related sequence on the C-terminal side of the amino acid sequence (SEQ ID No: 2) of the fourth transmembrane region from the N-terminal of human CMTM4 (SEQ ID No: 46).

Sample 5 was designed as a comparative example and was a synthetic peptide including the amino acid sequence (LIM kinase 2) of SEQ ID No: 38 as the CPP-related sequence on the C-terminal side of a signal peptide of a human complement factor B (SEQ ID No: 47).

Table 1: The Amino Acid Sequences of the Synthetic Peptides Tested

TABLE 1

Table 1: Test sample peptide

| Sample No. | Amino acid sequence | Number of amino acid residues | SEQ ID No: |
|---|---|---|---|
| 1 | VAQVILALIAFICIETIMACSKKRT LRKNDRKKR | 34 | 43 |
| 2 | YFFEFVSCSAFVVTGVLLIMFKKRT LRKNDRKKR | 34 | 44 |
| 3 | LVNTGLSAFLFFIASIVLAALKKRT LRKNDRKKR | 34 | 45 |
| 4 | IAAVIFGFLATAAYAVNTFLAKKRT LRKNDRKKR | 34 | 46 |
| 5 | MGSNLSPQLCLMPFILGLLSGGVTT KKRTLRKNDRKKR | 38 | 47 |

All of the peptides of Samples 1 to 5 were synthesized by performing a solid-phase synthesis method (Fmoc method) manually using a commercially available peptide synthesizer. Here, since a manner of use of the peptide synthesizer itself does not characterize the present invention, detailed description thereof will be omitted. Here, in all synthetic peptides shown in Table 1, in the peptide having an amino acid sequence of a corresponding sequence number, a carboxyl group (—COOH) of the C-terminal amino acid was amidated (—CONH$_2$).

The synthesized peptides of the samples were dissolved in dimethyl sulfoxide (DMSO), and stock solutions (with a concentration of 2.5 mM) containing the sample peptides were prepared.

Test Example 2: Evaluation Test (1) of Antitumor Activity of Synthetic Peptides

The antitumor activity of the peptides of Samples 1 to 4 synthesized in the above Test Example 1 was evaluated using human-derived cultured tumor cells as targets.

Specifically, currently commercially available human melanoma (A2058) cell lines were used as test tumor cells. In addition, a normal human mammary epithelial cell culture line (MCF-12F) was used for comparison. Here, culture solutions of respective cells are as follows.
(1) A2058 Cells:

A DMEM culture medium including 2 mM of L-glutamine, 0.1 mM of non-essential amino acids, 50 unit/mL of penicillin, 50 µg/mL of streptomycin, and 10% fetal bovine serum (FBS) (product, commercially available from Wako Pure Chemical Industries, Ltd.).
(2) MCF-12F Cells:

A DMEM/F12 culture medium including 20 ng/mL of recombinant EGF, 10 µg/mL of insulin, 0.5 µg/mL of hydrocortisone, and 10% FBS (product, commercially available from Wako Pure Chemical Industries, Ltd.).

Details of the test are as follows.

A2058 cells and MCF-12F cells were cultured and prepared so that the number of cells per well in a 96-hole (well) plate was about $5 \times 10^3$. An amount of the culture medium in this case was 100 µL per well.

Next, the 96-hole (well) plate was placed in a $CO_2$ incubator and pre-incubated under conditions of 37° C. and 5% $CO_2$ for about 1 day (21 hours to 24 hours).

Then, peptide-containing test culture mediums for each concentration were prepared so that the concentrations of the sample peptides to be evaluated were 6.25 µM, 12.5 µM, and 25 µM and supplied to wells (that is, wells after the pre-incubation) in which 90 µL of cells to be evaluated were cultured in each well. Then, the 96-hole (well) plate was returned to the $CO_2$ incubator and incubated under conditions of 37° C. and 5% $CO_2$ for 48 hours.

Here, the number of test wells (n) at peptide concentrations in peptide addition test groups was set to 6. Therefore, the value of the result shown in the following table is an average value of the results obtained in 6 test wells.

After the incubation for 48 hours was completed, the culture medium in each well was substituted with 100 µL of a fresh culture medium containing no peptide, and additionally, 10 µL of a cell proliferation measurement reagent "Cell Counting Kit-8" (product, commercially available from Dojindo Laboratories) containing a "water-soluble tetrazolium salt (WST-8)" as a coloring reagent was added to each well. Then, the 96-well plate was returned to the $CO_2$ incubator and incubated under conditions of 37° C., and 5% $CO_2$ for 1.5 hours to 2 hours.

After the incubation was completed, the cell culture solution to which the reagent was added was collected and the cell viability (%) was calculated according to a colorimetric method in which an absorbance at a wavelength of 450 nm (value corrected by the absorbance at a wavelength of 620 nm: A450-A620) was measured based on the reduction of the tetrazolium salt. Specifically, a measured value (measurement absorbance) of a comparative test group in which the above incubation was performed for 48 hours in a culture medium containing no sample peptide was set as a cell viability of 100%. Then, the viability A (%) of A2058 cells and the viability B (%) of MCF-12F cells were calculated. In addition, an antitumor index was calculated based on the viability of A2058 cells and MCF-12F cells using the above Formula (1), and thus the antitumor activity of the sample peptide with respect to A2058 cells was evaluated. The results are shown in Table 2.

TABLE 2

Antitumor index

| Test cell lines | Test sample No. | Peptide treatment concentration | | |
|---|---|---|---|---|
| | | 6.25 μM | 12.5 μM | 25 μM |
| Melanoma (A2058) | 1 | 1.17 | 0.71 | 0.74 |
| | 2 | 0.79 | 0.61 | 0.52 |
| | 3 | 0.15 | — | — |
| | 4 | 0.84 | 0.65 | 0.12 |
| Melanoma (SK-MEL5) | 3 | 0.16 | — | — |

As can be clearly understood from the results shown in Table 2, the synthetic peptides of Samples 1 to 4 reduced the proliferation of A2058 cells (that is, tumor cells). In addition, since the antitumor index based on the viabilities of A2058 cells and MCF-12F cells of Sample 3 and Sample 4 among Samples 1 to 4 had a smaller value than that of the other samples, it was confirmed that the antitumor compositions containing the synthetic peptides of Sample 3 and Sample 4 had stronger antitumor activity. In addition, the antitumor activity of Sample 3 was significantly better than that of the other samples. Here, under the treatment with 6.25 μM of Sample 3, the antitumor index based on the viabilities of A2058 cells and MCF-12F cells was less than 0.2. As described above, since Sample 3 exhibited excellent antitumor activity even with a low treatment concentration, the test under the treatment with 12.5 μM and 25 μM of Sample 3 was not performed. That is, "-" in Table 2 indicates that no test was performed.

It is known that A2058 cells are highly malignant in human melanoma cell lines and are resistant to many antitumor compositions. However, all of the above sample peptides exhibited excellent antitumor activity (tumor cell growth inhibitory activity) with respect to such melanoma cell lines.

Test Example 3: Evaluation Test (2) of Antitumor Activity of Synthetic Peptides

The antitumor activity of Sample 3 in the above Test Example 1 was evaluated using human melanoma cell line different from A2058 cell line as a target.

Specifically, currently commercially available human melanoma cell line (SK-MEL5) were used as a test tumor cell line. In addition, the above MCF-12F cells were used for comparison.

The following culture medium was used for culturing SK-MEL5 cells.

That is, an E-MEM culture medium (product, commercially available from Wako Pure Chemical Industries, Ltd.) containing 1 mM of sodium pyruvate, 100 unit/mL of penicillin, 100 μg/mL of streptomycin, and 10% FBS.

Details of the test were as those described in Test Example 2. The antitumor index based on the viabilities of SK-MEL5 cells and MCF-12F cells calculated using the above Formula (1) is shown in the above Table 2.

As can be clearly understood from the results shown in Table 2, the synthetic peptide of Sample 3 significantly reduced proliferation of SK-MEL5 cells (that is, tumor cells). This indicates that the synthetic peptide of Sample 3 can be applied to the synthetic peptide disclosed here regardless of the species of melanoma. Here, under the treatment with 6.25 μM of Sample 3, the antitumor index based on the viabilities of SK-MEL5 cells and MCF-12F cells was less than 0.2. As described above, since Sample 3 exhibited excellent antitumor activity even with a low treatment concentration, the test under the treatment with 12.5 μM and 25 μM of Sample 3 was not performed. That is, "-" in Table 2 indicates that no test was performed.

Test Example 4: Evaluation Test (3) of Antitumor Activity of Synthetic Peptides

The antitumor activity of Sample 3 and Sample 4 in the above Test Example 1 was evaluated using different tumor cells as targets.

Specifically, currently commercially available human kidney cancer cell lines (CAKI2) were used as test tumor cells. In addition, the above MCF-12F cells were used for comparison.

The following culture medium was used for culturing CAKI2 cells.

That is, a McCoy's 5A culture medium (product, commercially available from Gibco) containing 2 mM of L-glutamine, 3,000 mg/L of glucose, 100 unit/mL of penicillin, 100 μg/mL of streptomycin, and 10% fetal bovine serum (FBS).

Details of the test were as those described in Test Example 2. The antitumor index based on the viabilities of CAKI2 cells and MCF-12F cells calculated using the above Formula (1) is shown in Table 3.

TABLE 3

Antitumor index

| Test cell lines | Test sample No. | Peptide treatment concentration | | |
|---|---|---|---|---|
| | | 6.25 μM | 12.5 μM | 25 μM |
| Kidney cancer (CAKI2) | 3 | 0.77 | 0.10 | — |
| | 4 | 1.41 | 0.83 | 0.22 |

As can be clearly understood from the results shown in Table 3, the synthetic peptides of Sample 3 and Sample 4 significantly reduced proliferation of CAKI2 cells (that is, tumor cells). This indicates that the synthetic peptide of Sample 3 can be applied to the synthetic peptide disclosed here regardless of the species of tumor cells. Here, under the treatment with 12.5 μM of Sample 3, the antitumor index based on the viabilities of CAKI2 cells and MCF-12F cells was 0.1. As described above, since Sample 3 exhibited excellent antitumor activity even with a low treatment concentration, the test under the treatment with 25 μM of Sample 3 was not performed. That is, "-" in Table 3 indicates that no test was performed.

Test Example 5: Evaluation Test (4) of Antitumor Activity of Synthetic Peptides Using tumor cells as targets, the antitumor activity was evaluated using a synthetic peptide having a sequence completely different from those of Samples 1 to 4.

Specifically, the viability (%) of A2058 cells (tumor cells) when Sample 5 was treated was evaluated.

Details of the test were as those described in Test Example 2. Here, the viability of A2058 cells cultured in a culture medium containing no Sample 5 for the same time was set as 100%, and the viability (%) of A2058 cells cultured under the treatment of Sample 5 was calculated. The results are shown in Table 4.

TABLE 4

| | | Cell viability (%) | | |
|---|---|---|---|---|
| | Test | Peptide treatment concentration | | |
| Test cell lines | sample No. | 6.25 μM | 12.5 μM | 25 μM |
| Melanoma (A2058) | 5 | 110.7 | 109.9 | 113.6 |

As shown in Table 4, no antitumor activity was exhibited in Sample 5. That is, it was confirmed that the antitumor activity was specific to the amino acid sequences of Samples 1 to 4. Then, it was confirmed that the synthetic peptide according to Sample 5 could be used, for example, as a control peptide in an evaluation test for antitumor activity.

In the above test examples, the test was performed using human-derived tumor cells. However, it was confirmed that excellent antitumor activity of Samples 1 to 4 exhibited using tumor cells derived from non-human mammals as targets. In addition, it was confirmed that, even if the CMTM4-TM-related sequence was composed of a sequence derived from non-human mammals, excellent antitumor activity exhibited with respect to various tumor cells.

As described above, according to the synthetic peptide disclosed here, it is possible to inhibit (or suppress) proliferation of tumor cells. Therefore, when the synthetic peptide provided according to the present invention is used, it is possible to provide an antitumor composition (antitumor agent) that inhibits proliferation of at least one species of tumor cells.

The invention claimed is:

1. A synthetic peptide which inhibits proliferation of at least one species of tumor cells, consisting of the following amino acid sequences (1) and (2):
   (1) an amino acid sequence consisting of any one of SEQ ID NOs: 1, 2, and 4 and
   (2) an amino acid sequence consisting of any one of SEQ ID NOs: 25 to 42.

2. The synthetic peptide according to claim 1, wherein the amino acid sequence (1) is conjugated on the N-terminus or the C-terminus of the amino acid sequence (2) and, optionally, further comprising a linker consisting of 10 or less amino acid residues between amino acid sequence (1) and amino acid sequence (2).

3. The synthetic peptide according to claim 1, consisting of any one of SEQ ID NOs: 43, 44, and 46.

4. An antitumor composition inhibiting proliferation of at least one species of tumor cells, comprising:
   the synthetic peptide according to claim 1; and
   at least one pharmaceutically acceptable carrier.

5. A method of inhibiting proliferation of at least one species of tumor cells, comprising,
   supplying the synthetic peptide according to claim 1 to target tumor cells in vitro or in vivo at least once.

6. A synthetic peptide which inhibits proliferation of at least one species of tumor cells, consisting of the following amino acid sequences (1) and (2):
   (1) an amino acid sequence consisting of SEQ ID NO: 3 and
   (2) an amino acid sequence consisting of any one of SEQ ID NOs: 25 to 42.

7. The synthetic peptide according to claim 6, wherein the amino acid sequence (1) is conjugated on the N-terminus or the C-terminus of the amino acid sequence (2).

8. The synthetic peptide according to claim 7, consisting of an amino acid sequence consisting of SEQ ID NO: 45.

* * * * *